United States Patent
Lagoviyer et al.

(10) Patent No.: US 6,465,010 B1
(45) Date of Patent: Oct. 15, 2002

(54) MEANS FOR CREATING A MASS HAVING STRUCTURAL INTEGRITY

(75) Inventors: Yury Lagoviyer, St. Louis; R. Saul Levinson, Chesterfield; Denis Stotler, Richmond Heights; Thomas C. Riley, Manchester, all of MO (US)

(73) Assignee: Drugtech Corporation, Wilmington, DE (US)

( * ) Notice: Subject to any disclaimer, the term of this patent is extended or adjusted under 35 U.S.C. 154(b) by 0 days.

(21) Appl. No.: 09/902,751

(22) Filed: Jul. 12, 2001

Related U.S. Application Data

(63) Continuation of application No. 09/366,686, filed on Aug. 4, 1999, now Pat. No. 6,284,270.

(51) Int. Cl.⁷ ................................................. A61K 9/20
(52) U.S. Cl. .................... 424/464; 424/465; 514/772.3; 514/774; 514/960; 514/961
(58) Field of Search ................................ 424/464, 465, 424/441, 489, 469, 470, 435, 439

(56) References Cited

U.S. PATENT DOCUMENTS

| | | |
|---|---|---|
| 2,887,437 A | 5/1959 | Klioze et al. |
| 3,885,026 A | 5/1975 | Heinemann et al. |
| 4,590,075 A | 5/1986 | Wei et al. |
| 4,642,903 A | 2/1987 | Davies |
| 4,824,681 A | 4/1989 | Schobel et al. |
| 4,832,956 A | 5/1989 | Gergely et al. |
| 4,994,260 A | 2/1991 | Källstrand et al. |
| 5,064,656 A | 11/1991 | Gergely et al. |
| 5,073,374 A | 12/1991 | McCarty |
| 5,112,616 A | 5/1992 | McCarty |
| 5,126,151 A | 6/1992 | Boder et al. |
| 5,178,878 A | 1/1993 | Wehling et al. |
| 5,223,264 A | 6/1993 | Wehling et al. |
| 5,262,171 A | 11/1993 | Login et al. |
| 5,330,763 A | 7/1994 | Gole et al. |
| 5,464,632 A | 11/1995 | Cousin et al. |
| 5,501,858 A | 3/1996 | Fuisz |
| 5,501,861 A | 3/1996 | Makino et al. |
| 5,503,846 A | 4/1996 | Wehling et al. |
| 5,558,880 A | 9/1996 | Gole et al. |
| 5,587,172 A | 12/1996 | Cherukuri et al. |
| 5,587,179 A | 12/1996 | Gergely et al. |
| 5,607,697 A | 3/1997 | Alkire et al. |
| 5,622,719 A | 4/1997 | Myers et al. |
| 5,631,023 A | 5/1997 | Kearney et al. |
| 5,635,210 A | 6/1997 | Allen, Jr. et al. |
| 5,648,093 A | 7/1997 | Gole et al. |
| 5,720,974 A | 2/1998 | Makino et al. |

Primary Examiner—James M. Spear
(74) Attorney, Agent, or Firm—Nath & Associates PLLC; Gary M. Nath; Joshua B. Goldberg

(57) ABSTRACT

The present invention relates to a means for creating a mass having structural integrity, including a rapidly disintegratable tablet for administration with or without the use of water. The present invention has a wide variety of different uses and applications. One embodiment is a tablet intended for oral administration. The tablet comprises at least one active ingredient and a mixture of excipients. The excipients provide desired characteristics and physical properties and when the tablet is sintered or heated, excellent tablet binding characteristics are obtained. The tablet is intended primarily for oral administration and dissolves in the presence of water. Also disclosed is a process for the preparation of a rapidly disintegratable tablet for administration with or without the use of water. The process comprising dissolving at least one bulking agent and at least one structural agent in a suitable solvent, wherein the solvent provides high porosity upon drying; spray-drying or dispersing said dissolved mixture to obtain a bead or granulated product; dry blending at least one binding agent, and at least one active ingredient with the bead or granulated product to obtain a preformulation product or adding at least one active ingredient to the preformulation product dissolved or dispersed components before spray-drying or dispersing; compressing the preformulation product; and sintering or heating the preformulation product for a sufficient time and temperature to allow the binding agent to change status or melt and allow the binding agent to resolidify as the temperature is reduced to ambient temperature.

11 Claims, 1 Drawing Sheet

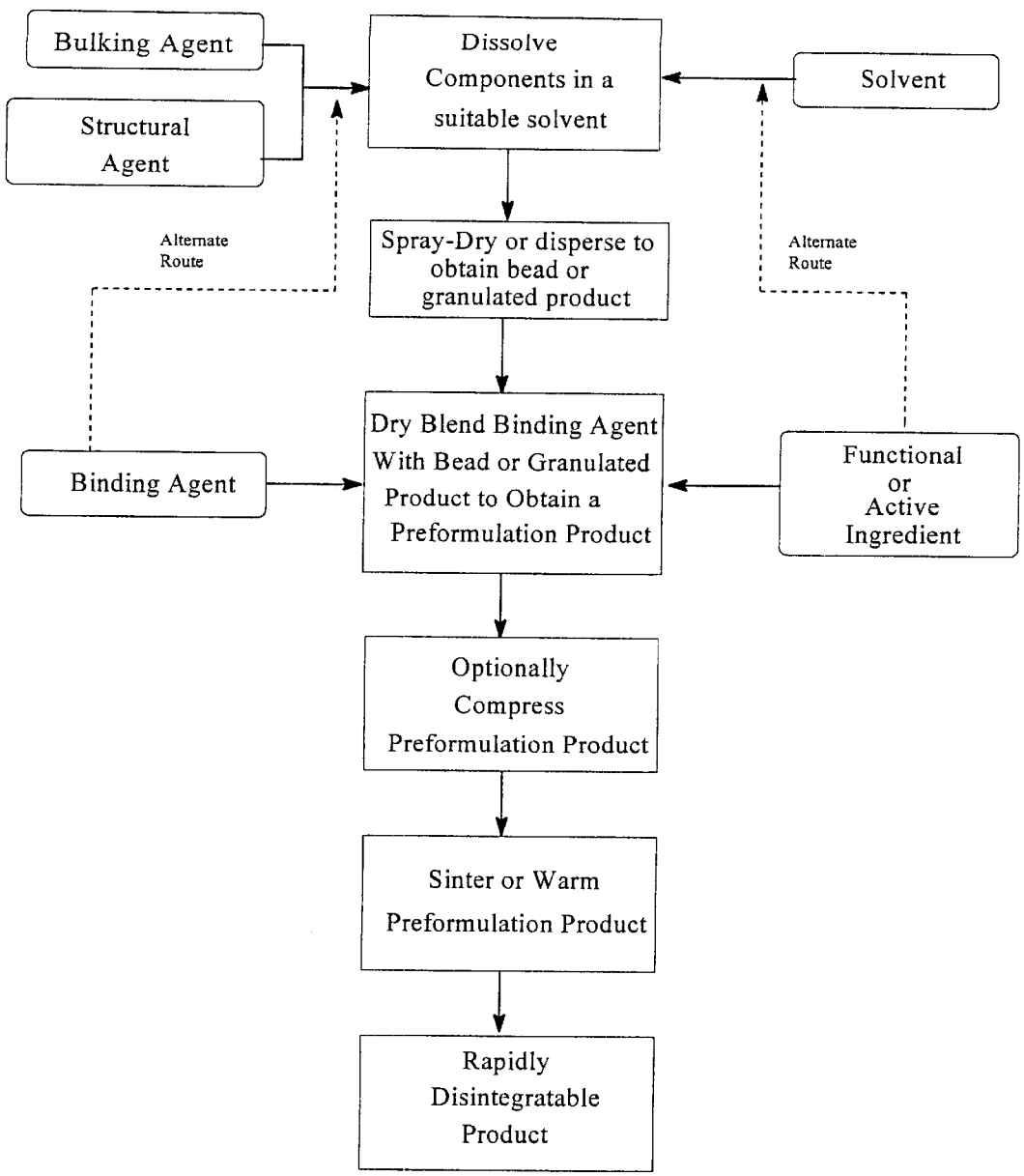
Figure

MEANS FOR CREATING A MASS HAVING STRUCTURAL INTEGRITY

This application is a continuation application of U.S. patent application Ser. No. 09/366,686, filed Aug. 4, 1999 now U.S. Pat. No. 6,284,270, the entire contents of which are hereby incorporated by reference in their entirety.

FIELD OF THE INVENTION

The present invention relates to a quick dissolving or disintegrating solid product or dosage form intended for a wide variety of uses, including oral administration to a patient to achieve a desired therapeutic response.

BACKGROUND OF THE INVENTION

Patient compliance remains a significant problem in health care. Compliance is dependent on a number of factors including but not limited to the route and frequency of drug administration. Frequency of administration can sometimes be decreased by administering long-acting, sustained release, or controlled release pharmaceutical formulations. These techniques have been of tremendous benefit, especially for oral administration. However, oral dosage forms themselves oftentimes have serious disadvantages that adversely affect patient compliance.

Oral dosage forms remain a significant problem for a significant segment of the population. Many patients are unable or unwilling to swallow a solid dosage form. This problem occurs primarily in children and the elderly, however, problems with swallowing are not limited to those segments of the population. Certain conditions or disease states manifest themselves by swallowing difficulties. Otherwise healthy individuals can also exhibit problems with swallowing. Such swallowing difficulties irrespective of their cause can severely compromise patient compliance. In addition, swallowing difficulties are not limited to humans and swallowing remains a significant issue in medicating animals.

The pharmaceutical industry has long-recognized the need for a form of oral administration which avoids the swallowing difficulties associated with a traditional tablet. Syrups, elixirs, microcapsules containing slurries, chewable tablets and other novel tablet or capsule dosage forms have been developed. None of these dosage forms have been ideal and each has their own disadvantages. The disadvantages include a more costly process for preparation and/or more costly packaging materials.

A number of researchers have described a wide variety of techniques for obviating or minimizing swallowing problems. Aikire et al, U.S. Pat. No. 5,607,697 discloses an oral dosage form which is composed of a plurality of microparticles each having a core including an active ingredient and a compound which is sweet in taste and has a cooling sensation. Such a compound can be selected from the group consisting of mannitol, sorbitol, a mixture of artificial sweetener and menthol, a mixture of a sugar and menthol or methyl salicylate.

Another solution to this problem was described in Wehling et al., U.S. Pat. No. 5,178,878 which relates to certain effervescent dosage forms containing microparticles. The effervescent dosage forms of Wehling et al. provide an effervescent dosage form for direct oral administration. The dosage form is designed to disintegrate rapidly in the mouth releasing its microparticles as a slurry for ingestion. The dosage forms produced in accordance with Wehling et al. can be placed in the patient's mouth and the effervescence contained therein can be activated on contact by the patient's saliva. The tablet then disintegrates.

Källstrand, et al., U.S. Pat. No. 4,994,260 relates to a pharmaceutical mixture. The mixture is used for the controlled release of a substance. According to Källstrand, et al., a liquid dosage form is produced using either a dry powder or microcapsules which are suspended in a solution of a release-controlling substance, also referred to as a "sink." Alternatively, it is possible to encapsulate the release-controlling substance, together with a drug, within an encapsulating shell. The release-controlling substance may include, inter alia, carbohydrates and carbohydrate-related compounds, disaccharides, monosaccharides, glycerol, glycol, glycosides of monosaccharides and substances derived from ethylene glycol.

Boder et al., U.S. Pat. No. 5,126,151 relates to an encapsulation mixture. Boder et al. refers to the construction of gums and candies in oral dosage forms. According to Boder et al., microcapsules are produced using a core material which can be selected from a wide variety of materials including sweeteners, medicaments, drugs, flavoring agents and the like. These materials can be used, either singularly or in combination, in either a single or multiple part delivery system. That is, one or more of these materials may be present within one coating matrix or may be separately coated by the matrix and employed alone or in combination in the final product. The resulting formulations are said to provide a masking of unpleasant tasting drugs such as potassium chloride and the like, thereby making consumption of the drug more appealing to the patient. The dosage forms may be prepared in chewable tablet form.

Also of interest may be Schobel et al., U.S. Pat. No. 4,824,681, and Wei et al., U.S. Pat. No. 4,590,075. Encapsulated sweeteners have also been used to provide an extended release of sweetening in, for example, chewing gum.

Cousin et al., U.S. Pat. No. 5,464,632 discloses a rapidly disintegratable tablet for oral administration with or without the use of water. The tablet comprises an active substance and a mixture of excipients, wherein the active substance is multiparticulate and in the form of coated microcrystals, coated microgranules or uncoated microgranules and wherein the mixture of excipients comprises excipients which are responsible for the disintegration. The tablet is intended to be swallowed and disintegration occurs in less than sixty seconds under the action of excipients which are responsible for disintegration and which are selected from the group consisting of at least one disintegrating agent and at least one swelling agent.

Cherukuri et al., U.S. Pat. No. 5,587,172 is directed to a comestible unit which disperses quickly in the mouth and is prepared by subjecting a feedstock comprising a carbohydrate capable of undergoing flash-flow processing without use of a solution to provide a shearform matrix; initiating crystallization of the shear/form matrix; forming flowable compactible micro-particulates by combining an additive with the shearform matrix; and compacting the micro-particulates to form the final unit.

Gole et al., U.S. Pat. No. 5,558,880 is concerned with a method for preparing a solid, porous delivery matrix comprising a porous network of matrix material that disperses rapidly in water. The matrix material comprises a matrix forming agent and one or more amino acids having from about 2 to 12 carbon atoms. The matrix material dispersion is then lyophilized or subjected to solid-state dissolution to form the solid, porous delivery matrix.

A number of companies have attempted to develop a quick dissolving oral tablet using lyophilization techniques. A number of disadvantages are also associated with those products. First, water-dissolving compounds interfere with the freeze-dry cycle. Second, the product oftentimes has an unpleasant or bad taste and, third, the lyophilization process itself is time-consuming and expensive. A lyophilized formulation cannot be used with water soluble active ingredients and is limited to low dosages of active ingredients. Further, these tablets are very fragile requiring special packaging procedures thereby increasing the cost of the final product.

Yet another manufacturer uses effervescence to create a quick dissolving tablet. Carbon dioxide is generated within the tablet in order to blow the tablet apart. Once again, the tablets prepared by this process are very fragile and require special and costly packaging procedures.

Another manufacturer utilizes spun sucrose ("cotton candy") as a quick dissolving tablet matrix. This is an undesirable technology because of the hydroscopic nature of spun sucrose. The resultant tablets are very fragile and require special packaging.

Yet others have dissolved a preparation of a 3% gelatin bead using a spray-dried process. This is not very efficient in terms of throughput. Animal gelatin and sugars are used to prepare a spray-dried bead which is mixed with other ingredients and tablets are stamped out using a tableting machine.

There remains a need in the art for quick dissolving oral tablets, i.e., tablets which dissolve and/or disintegrate, without the need for water or a liquid, in the mouth of a patient. Water or another suitable liquid may not be convenient or readily available or a patient may experience difficulty swallowing. In either situation it would be desirable to use a tablet which can incorporate a large amount of an active ingredient or drug optionally along with taste-masking excipients and also the release of the active ingredient upon contact with the surface of the mouth.

Thus, while the art has long-struggled with developing a more desirable oral pharmaceutical dosage form, there remains a long-felt need for an improved oral dosage form.

An object of the present invention is to develop a relatively quick dissolving or disintegrating oral dosage form that disintegrates in the mouth within approximately 60 seconds, preferably less than ten seconds, and has acceptable mouth feel.

A further object of the present invention is to develop a tablet for oral administration with superior taste, convenient administration and a high load of active ingredient per unit dose without the need for expensive packaging procedures.

It is also a primary object of the present invention to prepare a finished product which readily disintegrates or dissolves upon exposure to an aqueous environment. Such a product would be especially useful in a wide variety of applications, including but not limited to the delivery of pharmaceutical products to a patient, including sterile ophthalmic solutions, food application, such as confections including a nugget bar or the like, veterinary uses including a chunk of material intended to be licked by an animal: cosmetics, diagnostics, sanitation of water or water products, carriers for pigments (paint), dispersants for dyes, agricultural uses including fertilizers, herbicides and the like, preparation of a mold or model material and the like.

The mixture of excipients in the rapidly disintegratable tablet provide desirable mouthfeel characteristics and physical properties when the tablet is sintered. Further objects and embodiments of the present invention will be made known in the following description of the preferred embodiments and claims. Though the following description of the preferred embodiments focuses on the inclusion of pharmaceuticals as the active agents, it is to be understood that the desirable properties of the inventive methods and dosage forms may be advantageously used in connection with many different types of active agents.

SUMMARY OF THE INVENTION

In accordance with the present invention, there is provided a rapidly disintegratable or quick dissolving product which releases a functional or active ingredient upon exposure to an aqueous environment. The product comprises at least one functional or active ingredient and a mixture of excipients, wherein said excipients provide desired characteristics and physical properties such that when the product is sintered or heated, excellent binding characteristics are obtained.

There is also provided a rapidly disintegratable or quick dissolving product. This product is advantageously useful for administration with or without the use of water, said product comprising at least one functional or active ingredient and a mixture of excipients, wherein said excipients provide desired characteristics and physical properties such that when the product is sintered or heated, excellent binding characteristics are obtained. The product is preferably a tablet which is intended to disintegrate in the mouth or in the presence of an aqueous environment. The mixture of excipients in the rapidly disintegratable product preferably provide desirable mouthfeel characteristics and physical properties when the tablet is sintered or heated. The sintering or heating is preferably conducted at approximately 50° C. to 120° C. The mixture can contain at least one binding agent and the binding agent is preferably polyethylene glycol having a molecular weight of approximately 1,000 to 1 million. The rapidly disintegratable product preferably contains a structural agent, preferably gelatin, more preferably fish gelatin.

Applicants have also discovered a process for the preparation of a rapidly dissolvable or disintegratable tablet as described above for use with or without water. Release of the active ingredient simply requires exposure to an aqueous environment.

The process comprises dissolving at least one bulking agent and at least one structural agent in a suitable solvent, wherein said solvent provides high porosity upon drying; spray-drying or dispersing said dissolved mixture to obtain a granulated product which can also be referred to as a matrix or bead; dry blending at least one binding agent, and at least one active ingredient with the granulated product to obtain a preformulation product or adding at least one active ingredient to the dissolved components before drying; optionally compressing said preformulation to obtain a form such as a tablet; and sintering or heating said preformulation for a sufficient time and temperature to allow the binding agent to change status or melt and allow said binding agent to resolidify as the temperature is reduced to ambient temperature. The active ingredient may be added to the solvent, the dissolved components or the dry blended mixture. The binding agent may be added to the bulking agent, the structural agent, the combined bulking agent and structural agent or dry blended along with the bead or granulated product to obtain a preformulation product.

BRIEF DESCRIPTION OF THE DRAWINGS

The FIGURE provides a chart depicting a manufacturing process for preparing the quick dissolving product of the present invention.

DETAILED DESCRIPTION OF THE PREFERRED EMBODIMENTS OF THE INVENTION

The present invention involves the preparation of a quick dissolving porous structure without lyophilization by creating a porous formulation thereby avoiding many of the disadvantages associated with the prior art. While such a quick dissolving structure would be especially suitable for an immediate release formulation for pharmaceutical applications, it would also be useful for sustained and controlled release applications. In addition, while the invention would be especially suitable for administering drugs to humans, it is anticipated that a product prepared by these teachings would be suitable for administering drugs to animals and for other uses such as diagnostic test kits, cosmetics, water sanitation, carriers for pigments, agricultural uses, dye dispersions, flavor/sweetening dispersions, or medicinal agents for dispersion, and the like. Thus a wide number of uses are envisioned.

The present invention involves the formation of a spray-dried or dispersed granulation product also known as a matrix or bead wherein the bead or granulation product is incorporated in the formation of a preformulation product, optionally compressed, with the addition of binding and structural agents wherein said binding agent is activated with heat during a sintering or heating step.

One advantage of the present invention for pharmaceutical applications is that it can incorporate taste-masking technologies. Further, since the active ingredient, e.g., drug, can be added to the formulation in a dry state, a wide variety of different types of compounds or active ingredients can be used in the formulation. The active ingredient can also be placed in a suspension or slurry that can be spray-dried or dispersed independent of solubility. These are significant advantages associated with the practice of the present invention.

The finished product of the present invention can be used in a variety of ways. In particular, the product of the present invention is useful as a quick disintegrating or quick dissolving pharmaceutical formulation intended for a variety of routes of administration including intravenous, intramuscular, intraperitoneal, subcutaneous, oral, rectal, vaginal and the like. The oral route of administration would be most preferred.

However, the finished product of the present invention could also be used as a means to deliver a nutrient or it can be a diagnostic method, e.g., using monoclonal antibodies. Other uses include a means to deliver an insecticide or a fertilizer. Thus, a wide number of types of compounds and materials may be advantageously incorporated into the structural mass of the present invention. Whatever active ingredient is incorporated into the product of the present invention, it should be present in an effective amount per unit volume to achieve the desired effect.

The composition of the present invention can also carry a higher payload, i.e., a larger amount of active ingredient per unit dose while still maintaining a small unit size. In the case of pharmaceutical as well as other applications, the rapidly disintegratable product could take the form of a tablet, granules, bar, block, disc, or the like. For instance, for pharmaceutical applications, dosage ranges of up to 2,500 mg are possible, more likely 1,000 mg. Dosage ranges for the treatment of humans typically extend from approximately 2 mg to 500 mg, preferably 10 mg to 250 mg.

Much higher dosage units are also possible depending on the intended use and the size of the final rapidly disintegratable product. For instance, for water treatment applications, a large block could be placed in a lake.

The process of the present invention also advantageously avoids the significant time and expense associated with lyophilization. Lyophilization limits the amount of active ingredient to approximately 100 mg per unit dose, cannot incorporate active ingredients that exhibit high water solubility which interfere with the freezing process, and eliminates the use of drug candidates that are associated with an undesirable taste.

The process of the present invention is also advantageous because it does not rely on effervescence or carbon dioxide release since the amount of active ingredient is also limited in those processes because too much drug can interfere with the speed of the effervescence, and thereby affect the speed of dissolution/disintegration of the product.

The desirable quick dissolving dosage form of the present invention, when used as an oral pharmaceutical, dissolves or disintegrates rapidly in the mouth, generally within 3–60 seconds, preferably 10–30 seconds. The dosage form of the present invention also allows the incorporation of a wide range of dosage levels. The solubility or insolubility of the active ingredient or drug does prohibit the use of the present manufacturing process as is the case with the state of the art, particularly lyophilization. The formulation of the present invention can achieve individual benefits such as taste masking, preparation of controlled release forms, better stability, better separation, and the like.

The formulation of the present invention allows the production of a robust dosage form that can be packaged in a wide variety of packaging configurations such as bulk bottles, strip, blister and the like.

The process of the present invention provides an oral quick dissolving dosage form of one or more active ingredients or drugs in which taste masking can be incorporated, if desirable. The formulation is not limited to a specific class, category or type of active ingredient and allows for a wide range of such active ingredients or compounds, which can be either water soluble or water insoluble.

The quick dissolving dosage forms of the prior art tend to be fragile, cannot incorporate tastemasking, and/or cannot be developed for many drug agents. The subject technology addresses the limitations of the current technologies and allows the formulation of a much more acceptable quick dissolving oral dosage form.

In the realm of pharmaceutical use, pharmaceutical dosage forms prepared according to the present invention exhibit rapid dissolution upon contact with physiological solvents, such as water, saliva, or gastrointestinal fluids. Therefore, the present inventive pharmaceutical dosage forms provide a more rapid dispersion of the pharmaceutical within the body upon ingestion.

Embodiments of the present invention have the following potential applications:

Pharmaceutical

1. Dosage forms having mucoadhesive properties.
2. Dosage forms designed to deliver drug at a controlled rate.
3. Dosing units designed to deliver drugs in the eye.
4. Dosing units designed to deliver drugs in vaginal, rectal and other body orifices.
5. Solid dosage forms designed to replace liquid formulations.
6. Dry medicated preparations for topical application after resolution (reconstitution).

7. Preparation of medicated units or sheets for topical application.
8. Preparation of more palatable dosage forms of drugs that exhibit disagreeable organoleptic properties.
9. Dosage forms for oral delivery of drugs to persons who have difficulty swallowing tablets or capsules.
10. Immunizing kit.
11. Skin antigen.

Food

1. Preparation of and presentation of dried products composed of food materials.
2. To provide a method for the selective extraction of a material in the solid form during the drying process.
3. Preparation of confectionery products.
4. Preparation of dosing units for the purpose of modifying properties (e.g., taste, color, etc.) or quality of drinking water.

Veterinary

1. Preparation of dosing units for veterinary use.
2. Preparation of aquarium care and feed products.

Cosmetics

1. Preparation of dry systems for medical and cosmetic use after resolvation.

Diagnostic

1. Enzyme/cofactors and biochemical carrier systems.
2. In vitro test kit containing reagents.

Sanitary

1. Preparation of dosing units for water purification, for example, chlorine, pH, bacteriostatic and the like.
2. Preparation of fragrance carrier units for personal, household and industrial use.
3. Aquaculture as nutrients or medicinals.

Other

1. Reconstitutable carrier units for pigmented application for paint and other artistic uses.
2. Agriculture and horticulture products requiring release of active ingredients in the presence of water or rain.
3. Preparation of easily removable mold or model material.
4. Preparation of easily removable space maintenance and/or alignment aid for construction or manufacturing.
5. Aquaculture for feed for fish, shrimp, and the like.

In the practice of the present invention, a bulking agent is combined with a structural agent. Suitable bulking agents for use in the practice of the present invention include carbohydrates such as sucrose, mannitol, sorbitol, xylose, dextrose, fructose, mannose and the like, calcium carbonate, magnesium carbonate and the like. The amount of bulking agent useful in the practice of the present invention is an amount sufficient to provide bulk to the overall tablet formed and can range from approximately 10% to 95% of the entire composition.

The structural agent useful in the practice of the present invention can be a wide variety of materials. In the area of pharmaceutical sciences, it is preferably agar, gelatin, albumen, chondroitin and the like. The preferred structural agent is gelatin. The most preferred gelatin is fish gelatin. Fish gelatin is especially advantageous since it has a low bloom strength which allows a very high concentration of material on the spray-dried matrix or bead of the present invention. The fish gelatin is also advantageous because it eventually provides a porous support structure that allows the tablet to readily dissolve in the mouth. This is one of the preferred embodiments associated with the practice of the present invention.

There are other advantages associated with the use of fish gelatin as opposed to using regular gelatin. Regular gelatin can be derived from pigs or cows. Concerns relating to the preparation of kosher products or mad cow disease are eliminated by the use of fish gelatin. In addition, when regular gelatin having a 2 to 3% solids content gets into solution, it cannot be spray-dried because regular gelatin has a bloom strength of 100–300 and develops a viscosity that is too high for effective spray drying. Fish gelatin, on the other hand, has a bloom strength of only about 0–25 so the spray-drying process is thereby made more efficient.

The amount of gelatin useful in the practice of the present invention is an amount sufficient to provide structure or support to the tablet and can range from approximately 0.1% to 20%, preferably 1 to 3%.

The bulking agent/structural agent mixture is then dissolved in a solvent. Suitable solvents include water, ethyl alcohol, isopropyl alcohol, and the like, or a mixture thereof. The preferred solvent is a combination of ethyl alcohol and water in a ratio ranging from approximately 1:1 to 1:100. The solvent is present in an amount sufficient to provide the desired porosity to the bead or granulated product upon drying.

The bead or granulated product formed using one or more bulking agent and one or more structural agents ultimately allows a low density tablet to be formed and the granulated product can be readily prepared using a spray-dry or dispersing (including instantizing) procedure. Thus, the strength of the ultimate product is enhanced by blending the spray-dried or dispersed bead or granulated product with a binding agent along with the other active ingredients or components. Alternatively, when the active ingredient or compound is added to the solvent or dissolved components, a bead or granulated product can be spray-dried or dispersed while containing the active ingredient. Therefore, the active ingredient or drug can be introduced into the process in a number of ways.

The bead or granulated product is obtained using any spray-dry or dispersing technique known in the art. The spray-dry technique is preferred and is intended to produce a quick dissolving or rapidly disintegratable bead or granulated product. An instantizing technique may also be used to obtain the granulated product. The type of spray dry unit and the technique employed varies depending on the unit selected and can be readily determined by one skilled in the art in order to obtain the product of the present invention.

A binding agent can also be added to the spray-dried or dispersed granulated product along with the active ingredient. These three components can then be dry blended and optionally compressed, preferably under light compression, to form a tablet, bar, block, disc, or the like. These compressed tablets are then sintered to form a robust ultimate tablet. Alternatively, the binding polymer can be introduced along with the structural agent as well as the bulking agent and/or solvent. Thus the binding polymer may be introduced into the process in a number of ways.

In a variation of the present process, the active drug may be added to the spray-dried pretableting formulation in the alternative route depicted on the right of the Figure. That is, the pharmaceutically active agent or drug could be introduced before the spray-drying step, either along with the solvent or along with the bulking agent and structural agent in the solvent.

In yet another variation of the process, the binding agent as depicted on the left side of the Figure may be added along with the structural agent or bulking agent or, alternatively, the binding agent could be dissolved directly into the solvent in any order along with the bulking agent, structural agent and active ingredient. These variations of the process as well as other variations are well-known to those skilled in the art of pharmaceutical formulations.

Binders include starches, pregelatinized starches, gelatin, polyvinylpyrolidone, methylcellulose, sodium carboxymethylcellulose, ethylcellulose, polyacrylamides, polyvinyloxoazolidone, polyvinylalcohols and the like.

Preferred binding agents useful in the practice of the present invention includes polyethylene glycol; $C_{12}$–$Cl_{18}$ fatty acid alcohol, preferably stearyl alcohol; polypeptide; and the like. The polypeptide can be any arrangement of amino acids ranging from approximately 100 to 300,000 daltons. Any of the foregoing would be useful in the practice of the present invention. The preferred binding agent is polyethylene glycol (PEG) having a molecular weight of approximately 1,000 to 1,000,000. The PEG, preferably melts at about 50° C. to 90° C., and is intended to resolidify as the temperature of the final sintering or heating step decreases. PEG is water soluble and can function both as a binder and as a capillary attractant. The amount of binding polymer useful in the practice of the present invention is an amount sufficient to melt upon sintering or heating to provide rigidity or strength to the final product and can range from 0.5% to 25% of the weight of the final product.

The preformulated product can optionally be compressed. If it is not compressed, the granules can be sprinkled on the site of action or dropped into an aqueous environment.

Any technique used for compression would be useful in the practice of the present invention, including hand compression or the use of tableting equipment. Such tableting equipment is discussed in *Remington's Pharmaceutical Sciences*, which is hereby incorporated by reference, in its entirety herein.

The final step in the production of a quick dissolving/disintegrating tablet involves heat treating or sintering the compressed tablet. By sintering, the inventors mean any process incorporating energy in any form which results in heat transfer. Energy includes radiation or heat. The process of the present invention uses any form of energy which results in an increase in the adhesiveness or agglomerization of the granules (adhere together) so that the final product is stronger after the heat treatment than before. The heat treatment creates intratablet bonds and helps weld the product shape together. The heating can be conducted in an oven, a microwave, convection oven, or the like. Application of mechanical heat in any form is useful in the practice of the present invention. Typically, a laboratory oven is set at approximately 50° C. to 100° C. The heating time depends on the exact composition of the mixture but can extend anywhere from 1 minute to 12 hours, preferably 3 minutes to 45 minutes. The heating step is intended to melt the binding agent, such as a solid polyethyene glycol. More typically, the sintering is conducted at approximately 90° C. for approximately 10 minutes. The heat treating or sintering step improves the product's strength and durability thereby obviating the need for special packaging procedures and allows the product to be jostled during manufacture, shipping, and consumer use. Other means of heating/sintering can be employed and would be known to one familiar with industrial heating processes. Such heating processes as infrared heat, ultraviolet (UV) and other short wave radiation, microwave heat, radiant heat and industrial equipment designed with such attributes could be equally employed.

Any pharmaceutical agent or active ingredient would be useful in the practice of the present invention, such ingredients or agents include systemically distributable pharmaceutical ingredients such as, vitamins, minerals, dietary supplements, as well as nonsystemically distributable drugs.

Pharmaceutical ingredients may include, without limitation, antacids, analgesics, anti-inflammatory agents, antibiotics, antiviral agents, antiparasitic agents, laxatives, anorexics, antihistamines, antiasthmatics, bronchodilators, laxatives, antiflatulents, antimigraine agents, sedatives, antihyperactives, antihypertensives, tranquilizers, antidepressants, decongestants, beta blockers, $H_2$-antagonists, antitussives, decongestants, alkaloids, ion exchange resins, anti-cholesterolemics, anti-lipid agents, antiarrhythmics, antipyretics, appetite suppressants, expectorants, anti-anxiety agents, anti-ulcer agents, coronary vasodilators, cerebral dilators, peripheral vasodilators, anti-infectious agents, psychotropics, antimanics, neuroleptic agents, central nervous system stimulants, gastrointestinal agents, sedatives, antidiarrheal preparations, anti-anginal drugs, peripheral and brain vasodilators, anti-hypertensive drugs, vasoconstrictors, tranquillizers, antipsychotics, anti-tumor or anticancer drugs, anticoagulants, antithrombotic drugs, hypnotics, anti-emetics, anti-nausea agents, anticonvulsants, neuromuscular drugs, hyper- and hypoglycemic agents, thyroid and antithyroid preparations, diuretics, antispasmodics, uterine relaxants, antiobesity drugs, anabolic drugs, erythropoietin drugs, hematopoietical agents, uricosuric agents, plant extracts, contrast mediums, cough suppressants, mucolytics or mucoregulators, antiuricemic drugs, immunodepressant drugs, cholesterol lowering agents, hormones, enzymes, drugs acting on the rhythm of the heart, drugs used in the treatment of arterial hypertension, agents, drugs acting on blood coagulability, anti-epileptic agents, muscle relaxants, anti-Parkinson drugs, anorexigenic drugs, vitamins, minerals, dietary supplements, nutritional additives and mixtures thereof.

Especially preferred active ingredients contemplated for use in the present invention are antacids, $H_2$-antagonists, and analgesics. For example, antacid dosages can be prepared using calcium carbonate alone or in combination with magnesium hydroxide, and/or aluminum hydroxide. Moreover, antacids can be used in combination with $H_2$-antagonists.

Analgesics include aspirin, ibuprofen, naproxen, acetaminophen and the like with or without caffeine.

Other preferred drugs or active ingredients for use in the present invention include antidiarrheals such as Immodium AD, antihistamines, antitussives, decongestants, vitamins, and breath fresheners. Also contemplated for use herein are anxiolytics such as Xanax, antipsychotics, such as Clozaril and Haldol; non-steroidal anti-inflammatories (NSAID's), such as Voltaren and Lodine; antihistamines such as Seldane, Hismanal, Relafen, and Tavist; antiemetics, such as Kytril and Cesamet; bronchodilators such as Ventolin and Proventil; antidepressants, such as Prozac, Zoloft, and Paxil; antimigraines such as linigran, ACE-inhibitors, such as Vasotec, Capoten and Zeetril; anti-alzheimers agents, such as Nicergoline; and $Ca^{+2}$-Antagonists such as Procardia, Adalat, and Calan.

The popular $H_2$-antagonists which are contemplated for use in the present invention include cimetidine, ranitidine, famotidine, nizatidine, ebrotidine, mifentidine, roxatidine, pisatidine and aceroxatidine.

The active ingredients most useful in the practice of the present invention comprise ibuprofen, nitroglycerin, clarithromycin and azithromycin.

As used in this disclosure, the term vitamin refers to trace organic substances that are required in the diet. For the purposes of the present invention, the term vitamin(s) include, without limitation, thiamine, riboflavin, nicotinic acid, pantothenic acid, pyroxidine, biotin, folic acid, vitamin $B_{12}$, lipoic acid, ascorbic acid, vitamin A, vitamin D, vitamin E and vitamin K. Also included within the term vitamin are the coenzymes thereof. Coenzymes include thiamine pyrophosphates (TPP), flavin mononucleotide (FMM), flavin adenine dinucleotide (FAD), nicotinamide adenine dinucleotide (NAD), nicotinamide adenide dinucleotide phosphate (NADP), Coenzyme A (CoA), pyridoxal phosphate, biocytin, tetrahydrofolic acid, coenzyme $B_{12}$, lipoyllysine, 11-cis-retinal, and 1,25-dihydroxycholecalciferol. The term vitamin(s) also includes choline, carnitine, and alpha, beta, and gamma carotenes.

As used in this disclosure, the term mineral refers to inorganic substances, metals, and the like required in the human diet. Thus, the term mineral as used herein includes, without limitation, calcium, iron, zinc, selenium, copper, iodine, magnesium, phosphorus, chromium and the like, and mixtures thereof.

The term dietary supplement as used herein means a substance which has an appreciable nutritional effect when administered in small amounts. Dietary supplements include, without limitation, such ingredients as bee pollen, bran, wheat germ, kelp, cod liver oil, ginseng, and fish oils, amino acids, proteins and mixtures thereof. As will be appreciated, dietary supplements may incorporate vitamins and minerals.

In general, the amount of pharmaceutical ingredient incorporated in each tablet may be selected according to known principles of pharmacy. An effective amount of pharmaceutical ingredient is specifically contemplated. By the term effective amount, it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The amount of active agent used can vary widely from a few milligrams to 2500 milligrams or more. Of course, the size of the dosage form, the requirements of other ingredients, and the number of, for example, tablets which constitute a single dose will impact the upper limit on the amount of the pharmaceutically active ingredient which can be used. Generally, however between about 0.1 and 2,500 milligrams of active agent will be used in accordance with the present invention. More preferably between about 1 and about 500 milligrams and most preferably between and about 5 and about 250 milligrams of active agent are used. Stated another way, typically between about 0.1 and about 67% of the dosage form may be the active agent, based upon the weight of the finished dosage form. More preferably, the amount of active agent may vary from between about 0.6 and about 34% by weight based on the total weight of the finished dosage form. (A 750 mg tablet was used for this calculation.)

Other adjuvants may also be used in forming the quick dissolving/disintegrating tablet of the present invention or indeed, in formulating dosage forms as well. Adjuvants include, for example, calcium sulfate NF, dibasic calcium phosphate NF, tribasic calcium sulfate NF, starch, calcium carbonate, microcrystalline cellulose, modified starches, lactose, sucrose and the like, staRx, Avicel, Solka-Floc BW40 Alginic acid, Explotab, AUTOTAB, Guargum, Kaolin, Vecgum, Bentonite, and the like. In general, those may be used in up to 20% w/w, but often are used in amounts as low as 3–5% w/w.

In addition to the ingredients in accordance with the present invention, the dosage forms in accordance with the present invention may include flavors, diluents, colors, binders, fillers, compaction vehicles, non-effervescent disintegrants, and lubricants such as those disclosed in Wehling et al. Fragrances, dyes, sweeteners (both artificial and natural) and other additives may be present as well.

Flavors incorporated into the composition may be chosen from synthetic flavor oils and flavoring aromatics and/or natural oils, extracts from plants, leaves, flowers, fruits and so forth, and combinations thereof. These may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, apricot and so forth. Flavors may be present in an amount ranging from about 0.5 to 3.0 percent. Lubricants according to the present invention may be used in the amount of up to 20 weight percent, and preferably between 0.5 and about 4 weight percent based on the total composition.

Fillers may be used to increase the bulk of the tablet. Some of the commonly used fillers are calcium sulfate, both di- and tri-basic, starch, calcium carbonate, microcrystalline cellulose, modified starches, lactose, sucrose, mannitol, and sorbitol.

The sweeteners may be chosen from the following non-limiting list: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl- 1,2,3-oxathiazin-4-one-2,2-dioxide, particularly the potassium salt (acesulfame-K), and sodium and calcium salts thereof. Other sweeteners may also be used.

Lubricants are also useful in tableting formulations. Lubricants can include, but are not limited to, the following: magnesium stearate, calcium stearate, zinc stearate, hydrogenated vegetable oils, sterotex, polyoxyethyfene monostearate, talc, polyethyleneglycol, sodium benzoate, sodium lauryl sulfate, magnesium lauryl sulfate, light mineral oil and the like.

Furthermore, dispersion enhancers can optionally be used to enhance the breakability of the compressed tablet in an aqueous environment. The dispersants can include starch, alginic acid, polyvinylpyrrolidones, guar gum, kaolin, bentonite, purified wood cellulose, sodium starch glycolate, isoarnorphous silicate, and microcrystalline cellulose as high HLB emulsifier surfactants.

Other ingredients can also be used in the present invention include glidants such as starch, talc, magnesium and calcium stearate, zinc stearate, dibasic calcium phosphate, magnesium carbonate, magnesium oxide, calcium silicate, and silica arogels.

Also, color additives can be used in preparing tablets. Such color additives include food, drug and cosmetic colors (FD&C), drug and cosmetic colors (D&C), or external drug and cosmetic colors (Ext. D&C). These colors or dyes, along with their corresponding lakes, and certain natural and derived colorants are useful in the practice of the present invention. Lakes are dyes absorbed on aluminum hydroxide. Coloring agents may range from between 0.1 to 3.5 weight percent of the total composition.

One skilled in the art of formulations would know when to introduce the foregoing ingredients into the process. The most likely point of introduce would be during the dry blending step.

The present invention is a method of making tablets which disintegrate quickly in the mouth of a patient. The quick dissolving/disintegrating units or dosage forms produced in accordance with the present invention disintegrate/dissolve nearly instantaneously. However, these tablets are capable of being manufactured so that they can be handled for packaging and distribution without deterioration of the integrity of the product.

In the past, tablets have been made primarily by compressing feedstock under extremely high-pressure in order to provide the necessary hardness for handling required during packaging and distribution. Consequently, prior art tablets so produced were limited in that their high density reduces the capability of making them quickly disintegrate in the mouth. High density packing resulting from the high compression hinders the disintegration and wetting of the interior portion of the tablet.

As a result of the present invention, however, a significant step forward has been made in the art of preparing tablets which disintegrate very quickly in the mouth. In fact, tablets produced by the present invention can preferably disintegrate within seconds.

The foregoing will be better understood with reference to the following examples which detail certain procedures for manufacture of tablets in accordance with the present invention. All references made to these examples are for the purposes of illustration. They are not to be considered limiting as to the scope and nature of the present invention.

EXAMPLE 1

The goal of this example was to formulate, blend and tablet a quick dissolving tablet containing taste masked chlorpheniramine maleate as the active ingredient.

| Ingredient | Amount, g | % of Composition |
| --- | --- | --- |
| Chlorpheniramine Maleate, 10% | 1.4 | 7 |
| Spray Dried Matrix Bead | 14.12 | 70.6 |
| Polyethylene Glycol, PEG-3350 | 3.2 | 16 |
| Sweeteners | 0.6 | 3.0 |
| Cab-O-Sil | 0.14 | 0.7 |
| Coloring Agents | 0.1 | 0.5 |
| Flavors | 0.14 | 0.7 |
| Magnesium Stearate | 0.1 | 0.5 |

The target tablet weight was approximately 150 mg. The tablet was hand compressed using a ½inch round punch and die set. The mixture was blended for 10 minutes. The blend was compressed to produce a tablet having a weight of 150 mg.

Compressed tablets were sintered at 50° C. for 50 minutes in an oven. The tablets disintegrated in a USP Basket-Rack Assembly Disintegration Apparatus in about 10 seconds.

EXAMPLE 2

Chlorphenirarine maleate (CPM) was dissolved in the feed solution together with the other components of the tablet matrix. The solution was spray dried. The quick dissolving tablet matrix bead was produced. The bead contained 1.6% CPM.

| Ingredient | Amount, g | % of Composition |
| --- | --- | --- |
| Matrix with CPM | 231 | 76.0% |
| PEG-3350 | 30 | 9.9% |
| Tri-Calcium Phosphate | 36 | 12.0% |
| Cab-O-Sil | 3 | 1.0% |

The target tablet weight was approximately 570 mg. The tablet was compressed on a Stokes BB-2 tablet press, equipped with nine stations of a ½inch round flat beveled tooling. The mixture was blended for 3 minutes. The blend was compressed to produce a tablet having a weight of 570 mg.

Compressed tablets were sintered at 90° C. for 10 minutes in an oven. The tablets disintegrated in a USP Basket-Rack Assembly Disintegration Apparatus in under 15 seconds.

EXAMPLE 3

A quick dissolving formulation was prepared according to the present invention.

Spray drying of the tablet matrix was carried out in a spray dryer with an attached active carbon filter for solvent recovery.

The spray-dried matrix was processed as shown in the FIGURE and the tablets prepared sintered at 90° C., as also indicated in the FIGURE. The tablets prepared exhibited a robust nature in that they could be dropped on a table at a height of 2 feet without damage, and yet disintegrated in the mouth within 30 seconds.

Thus, while there had been described what are presently believed to be the preferred embodiments of the present invention, those skilled in the art will appreciate that other and further embodiments can be made without departing from the spirit of the invention and it is intended to include all such further modifications and changes as come within the true scope of the claims as set forth herein.

What is claimed is:

1. A rapidly disintegratable tablet for administration with or without the use of water, said tablet comprising a plurality of preformed beads, wherein the beads comprise at least one active ingredient and a mixture of excipients, said mixture of excipients consisting essentially of at least one bulking agent; at least one structural agent; at least one suitable solvent; at least one binding agent; and mixtures and combinations thereof, wherein said excipients provide desired characteristics and physical properties; wherein at least one binding agent is mixed with the preformed beads, said binding agent being polyethylene glycol, and when the tablet is sintered or heated, excellent tablet binding characteristics are obtained from the binding agent surrounding the preformed beads and binding them together; and wherein said structural agent is gelatin.

2. The rapidly disintegratable tablet according to claim 1, wherein said tablet is intended for oral administration.

3. The rapidly disintegratable tablet according to claim 2, wherein said tablet dissolves in the presence of water.

4. The rapidly disintegratable tablet according to claim 3, wherein said mixture of excipients provide desired mouth-feel characteristics and physical properties when the tablet is sintered.

5. The rapidly disintegratable tablet according to claim 1, wherein said polyethylene glycol has a molecular weight of approximately 1,000 to 1 million daltons.

6. The rapidly disintegratable tablet according to claim 1, wherein said gelatin is fish gelatin.

7. The rapidly disintegratable tablet according to claim 1, wherein said sintering or heating is conducted in the range of approximately 50° C. to 120° C.

8. The rapidly disintegratable tablet according to claim 1, wherein said active substance is selected from the group consisting of antacids, analgesics, anti-inflammatory agents, antibiotics, antiviral agents, antiparasitic agents, laxatives, anorexics, antihistamines, antiasthmatics, bronchodilators, laxatives, antiflatulents, antimigraine agents, sedatives, antihyperactives, antihypertensives, tranquilizers, antidepressants, decongestants, beta blockers, $H_2$-antagonists, antitussives, decongestants, alkaloids, ion exchange resins, anti-cholesterolemics, anti-lipid agents, antiarrhythmics, antipyretics, appetite suppressants, expectorants, anti-anxiety agents, anti-ulcer agents, coronary vasodilators, cerebral dilators, peripheral vasodilators, anti-infectious agents, psychotropics, antimanics, neuroleptic agents, central nervous system stimulants, gastrointestinal agents, sedatives, antidiarrheal preparations, anti-anginal drugs, peripheral and brain vasodilators, anti-hypertensive drugs, vasoconstrictors, tranquillizers, antipsychotics, anti-tumor or anticancer drugs, anticoagulants, antithrombotic drugs, hypnotics, anti-emetics, anti-nausea agents, anticonvulsants, neuromuscular drugs, hyper- and hypoglycemic agents, thyroid and antithyroid preparations, diuretics, antispasmodics, uterine relaxants, antiobesity drugs, anabolic drugs, erythropoietin drugs, hematopoietical agents, uricosuric agents, plant extracts, contrast mediums, cough suppressants, mucolytics or mucoregulators, antiuricemic drugs, immunodepressant drugs, cholesterol lowering agents, hormones, enzymes, drugs acting on the rhythm of the heart, drugs used in the treatment of arterial hypertension, anti-migraine agents, drugs acting on blood coagulability, anti-epileptic agents, muscle relaxants, anti-Parkinson drugs, anorexigenic drugs, vitamins, minerals, dietary supplements, nutritional additives and mixtures thereof.

9. The rapidly disintegratable tablet according to claim 8, wherein said active substance is selected from antacids, analgesics, anti-inflammatory agents, coronary vasodilators, peripheral vasodilators, antibiotics, antiviral agents, anti-anxiety drugs, central nervous system stimulants, antihistamines, hormones, anti-hypertensive agents, bronchodilators, anti-migraine agents, muscle relaxants, anti-epileptic agents, anti-Parkinson drugs, decongestants, diuretics, hypnotic/sedative drugs and expectorants.

10. The rapidly disintegratable tablet according to claim 9, wherein said active substance is selected from ibuprofen, nitroglycerin, clarithromycin and azithromycin.

11. A rapidly disintegratable product comprising a plurality of preformed beads, wherein the beads comprise at least one active ingredient and a mixture of excipients, said mixture of excipients consisting essentially of at least one bulking agent; at least one structural agent; at least one suitable solvent; at least one binding agent; and mixtures and combinations thereof, and wherein said excipients provide desired characteristics an physical properties; wherein at least one binding agent being polyethylene glycol, and when the product is sintered or heated, excellent binding characteristics are obtained from the binding agent surrounding the preformed beads and binding them together; and wherein said structural agent is gelatin.

* * * * *

UNITED STATES PATENT AND TRADEMARK OFFICE
CERTIFICATE OF CORRECTION

PATENT NO.     : 6,465,010 B1
DATED          : October 15, 2002
INVENTOR(S)    : Yury Lagoviyer et al.

It is certified that error appears in the above-identified patent and that said Letters Patent is hereby corrected as shown below:

<u>Column 16,</u>
Line 28, before the phrase "physical properties", delete the term "an" and replace with -- and --.
Lines 28-29, delete the phrase "wherein at least one binding agent being polyethylene glycol" and replace with the phrase -- wherein at least one binding agent is mixed with the preformed beads, said binding agent being polyethylene glycol --.

Signed and Sealed this

Fourth Day of February, 2003

JAMES E. ROGAN
*Director of the United States Patent and Trademark Office*